United States Patent [19]

Farng et al.

[11] Patent Number: 5,019,282

[45] Date of Patent: May 28, 1991

[54] ORGANIC ESTER, AMIDE OR AMINE SALTS OF PHOSPHORODITHIOATE SUBSTITUTE CARBOXYLIC ANHYDRIDES AS MULTIFUNCTIONAL ADDITIVES

[75] Inventors: Liehpao O. Farng, Lawrenceville; John P. Doner, Sewell; Andrew G. Horodysky, Cherry Hill, all of N.J.

[73] Assignee: Mobil Oil Corporation, Fairfax, Va.

[21] Appl. No.: 454,584

[22] Filed: Dec. 21, 1989

[51] Int. Cl.$^5$ .................................. C10M 137/10
[52] U.S. Cl. ........................ 252/32.7 E; 252/400.21; 252/389.21
[58] Field of Search ............. 252/32.7 E, 400.21, 252/389.21

[56] References Cited

U.S. PATENT DOCUMENTS

| | | | |
|---|---|---|---|
| 3,185,645 | 5/1965 | Clayton | 252/32.7 E |
| 3,192,162 | 6/1965 | Bartlett et al. | 252/46.6 |
| 3,284,354 | 11/1966 | Tunkel et al. | 252/32.7 E |
| 3,324,032 | 6/1967 | O'Halloran | 252/32.7 E |
| 4,784,780 | 11/1988 | Farng et al. | 252/32.7 E |
| 4,834,893 | 5/1989 | Doner et al. | 252/32.7 E |

*Primary Examiner*—Jacqueline V. Howard
*Attorney, Agent, or Firm*—Alexander J. McKillop; Charles J. Speciale; Howard M. Flournoy

[57] ABSTRACT

Certain organic ester, amide and amine salts of phosphorodithioate coupled carboxylic anhydrides have been found to be effective multifunctional antiwear and antioxidant additives for lubricants.

15 Claims, No Drawings

ORGANIC ESTER, AMIDE OR AMINE SALTS OF PHOSPHORODITHIOATE SUBSTITUTE CARBOXYLIC ANHYDRIDES AS MULTIFUNCTIONAL ADDITIVES

BACKGROUND OF THE INVENTION

This invention is directed to novel multifunctional antiwear and antioxidant additives and lubricant compositions containing same.

Lubricants, such as lubricating oils and greases are subject to oxidative deterioration at elevated temperatures or upon prolonged exposure to the elements. Such deterioration is evidenced, in many instances, by an increase in acidity and in viscosity. It can cause metal parts to corrode. Additionally, severe oxidation leads to a loss of lubrication properties. Improved antioxidants are clearly needed.

Antioxidants or oxidation inhibitors are used to minimize the effects of oil deterioration that occur when hot oil is contacted with air. The degree and rate of oxidation will depend on temperature, air and oil flow rates and, of particular importance, on the presence of metals that may catalytically promote oxidation.

Water (moisture) is another critical problem which can bring about ideal conditions for corrosion and damage of metal surfaces of materials in contact therewith. In the lubrication of internal combustion engines, for example, quantities of water are often present as a separate phase within the lubricating system. Another serious problem in respect to metallic surfaces in contact with adjacent metallic surfaces is the surface wear caused by the contact of such surfaces. The need for improving lubricity and providing antioxidant and antiwear additives for lubricating oils to meet the ever changing requirements of modern engines is clearly well known. One material capable of simultaneously effectively coping with these serious problems is highly desirous.

It has now been found that the use of phosphorodithioate derived succinic anhydride amide/ester/amine salt derivatives provide exceptional antioxidant and antiwear activity with significant rust inhibiting, and potential corrosion inhibiting properties.

The use of phosphorodithioate compositions, especially the corresponding salts of phosphorodithioate, such as zinc dialkylphosphorodithioates (commonly known as zinc dithiophosphates) have found widespread commercial use for several decades in engine oils as multifunctional antiwear, peroxide decomposing, and bearing corrosion inhibiting additives.

The use of succinic anhydride derivatives has been extensively reported as having beneficial antirust properties as well as detergency/dispersancy characteristics.

The herein disclosed remarkable benefits of the compositions in accordance with the present invention, are also expected for a variety of synthetic and mineral oil based lubricants. The compositions of matter and the lubricant compositions are believed to be novel. To the best of our knowledge, these compositions have not been previously used as multifunctional additives in lubricating oils, greases or fuel applications.

SUMMARY OF THE INVENTION

The invention is more particularly directed to lubricant compositions containing small additive concentrations of phosphorodithioate substituted hydrocarbyl or hydrocarbylene carboxylic anhydride-derived organic esters, amides and amine salts, such as (O,O-di-2-ethylhexyl-S-2-hydroxypropyl) phosphorodithioate substituted dodecenyl succinic acid diesters, amide esters and amine salts that possess excellent antioxidant properties coupled with very good antiwear and antirust activities. Both the phosphorodithioate alcohol moiety and the ester/amine/amide moiety are believed to provide the basis for the synergistic antioxidant activity and each of which are subsequently enhanced by the succinic anhydride coupling moiety. The phosphorodithioate group is believed to contribute additional antiwear properties to these novel additives.

The carboxylic anhydride moieties may additionally contribute significant antirust and/or anticorrosion properties to this new class of additives. All of these beneficial properties are believed to be enhanced as a result of this novel internal synergism.

This unique internal synergism concept is believed to be applicable to similar structures containing (a) amine/amide/ester groups, (b) phosphorodithioate derived alcohol groups, and (c) succinic acid/ester linkages, or phthalic acid/ester linkages, or related dibasic acid, diester groups within the same molecule.

Accordingly, it is an object of this invention to provide lubricant compositions of improved multifunctional capability having, e.g. antioxidant, antiwear and antirust/corrosion characteristics. It is a further object to provide novel additive products derived from phosphorodithioate substituted hydrocarbyl or hydrocarbylene or alkenyl carboxylic anhydride-derived organic esters, amides and amine salts thereof.

DESCRIPTION OF PREFERRED EMBODIMENTS

O,O-Dialkyl phosphorodithioic acids (made by the reaction of alcohols with phosphorus pentasulfide) or O,O-diaryl phosphorodithioic acids (made by the reaction of phenols, naphthols or similar aromatics with phosphorus pentasulfide) were reacted with alkylene oxides or hydrocarbyl epoxides to form phosphorodithioate-derived alcohols. However, any suitable method of preparation may be used.

These alcohols may then be reacted with carboxylic anhydrides (substituted succinic or phthalic anhydrides) to form dibasic acid esters, or diesters, as generally described below:

$$ROH + P_2S_5 \rightarrow (RO)_2PSSH \qquad \text{Equation 1}$$

where R is about $C_3$ to about $C_{30}$ hydrocarbyl or $C_3$ to about $C_{30}$ hydrocarbyloxyhydrocarbylene or mixtures thereof and can optionally contain sulfur, nitrogen and/or oxygen.

Equation 2

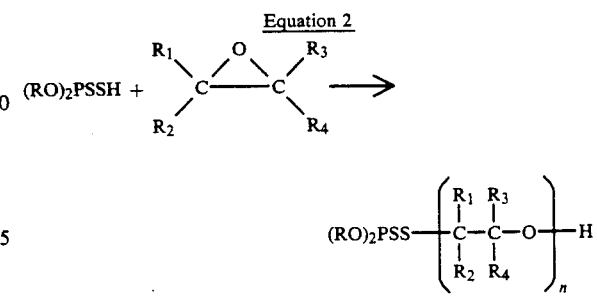

where $R_1$, $R_2$, $R_3$ and $R_4$ are hydrogen or $C_1$ to about $C_{30}$ hydrocarbyl, and can optionally contain sulfur, nitrogen and/or oxygen, $n=1$ to about 20.

Equation 3

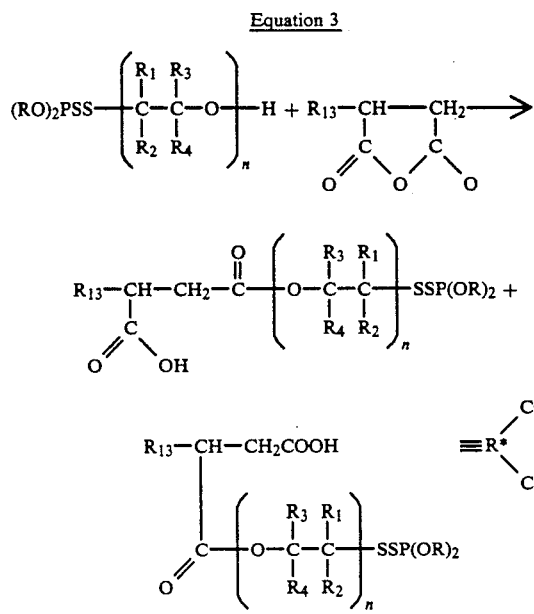

where $R^*$ represents the hydrocarbyl moiety, such as alkenyl substituted succinic (dibasic) moiety, and $R'$ represents the phosphorodithioate derived moiety.

Where $R_5$ $R_6$, $R_7$ and $R_8$ each are independently hydrogen or hydrocarbyl groups of $C_1$ to about $C_{10}$; and $R_9$ equals hydrocarbon based groups of $C_1$ to about $C_{60}$ and where $R_{13}$ is $C_1$ to $C_{30}$ hydrocarbyl or hydrocarbylene or

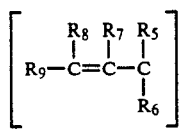

Unless otherwise specfied hydrocarbyl as used herein includes alkyl, alkenyl, cycloakyl, aryl, aralkyl or alkaryl groups which may have substituted thereon other groups, e.g., alkoxyl or alkylthio groups, etc. A given hydrocarbyl group may optionally contain sulfur, oxygen or additional nitrogen moieties or boron.

Suitable phosphorodithioates preferentially include O,O-di-2-ethylhexyl-S-(2-hydroxypropyl)phosphorodithioate, O,O-di-4-methyl-2-pentyl-S-(2-hydroxypropyl)phosphorodithioate, O,O-di-2-butyl-S-(2-hydroxypropyl-phosphorodithioate, O,O-di-2-methyl-1-propyl-S-(2-hydroxypropyl)phosphorodithioate.

Suitable esters amides/amines, preferentially include dodecenyl succinic acid ester, dodecenyl succinic anhydride-aniline adduct, dodecenyl succinic anhydride-mixed $C_{12}$-$C_{14}$ alkylamine adduct, dodecenyl succinic anhydride-bis(2-ethylhexyl) amine adduct, dodecenyl succinic anhydride-dibutyl amine adduct, dodecenyl succinic anhydride -$C_{12}$ (bis-2-hydroxyethyl cocoamine) and dodecenyl succinic anhydride-polyoxyalkylene amine adduct.

These substituted succinic acid-ester derivatives are subsequently converted to their corresponding diester, amide-ester, amine salts by reaction with almost molar quantities, or less than molar quantities, or more than molar quantities of amines or hydroxy compounds to make neutral, acidic, or basic derivatives (Equation 4). Generally, amines used in this invention can be alkylamines or arylamines; and hydroxy compounds used in the reactions can be phenols, alcohols and hydroxyesters.

Equation 4

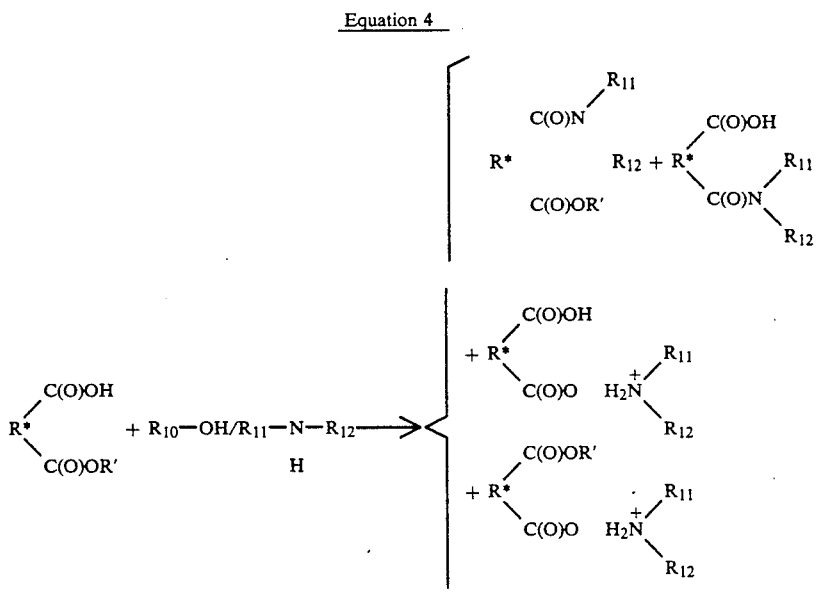

-continued

Equation 4

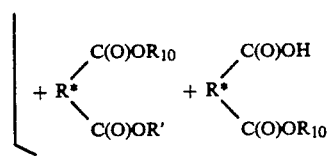

+ others where
$R_{10}$ equals hydrocarbon based groups of $C_1$ to about $C_{60}$ or oxygen, nitrogen, sulfur, boron-containing hydrocarbyl groups of $C_1$ to about $C_{60}$.

$R_{11}$ and $R_{12}$ equal hydrogen or hydrocarbyl groups of $C_1$ to about $C_{30}$, or hydrocarboxy hydrocarbylene groups; and R* and R' are as defined above.

Generally speaking the various reaction times, temperatures, pressures and quantities of reactive materials may vary widely and are not believed to be critical. However, an excess of one reagent or another may be used. The preferred stoichiometry is approximately equimolar under ambient conditions but up to a 200% excess of any reagent can be used, or as low as a 25% molar amount can be used. Thus 0.25 to 3 moles of any reagent can be used. The process can take place with or without a solvent or catalyst and up to 24 hours or more to complete.

The general reaction conditions may nevertheless be any suitable conditions known in the art. More specifically, reaction (2) preferably takes place at temperatures varying from about $-50°$ C. to about $150°$ C., at pressures varying from autogenous to ambient or slightly higher; reaction (3) is preferably carried out at temperatures ranging from about $20°$ to about $200°$ C., and in molar quantities ranging from about 10:1 to about 1:10 and preferably 1:1 and reaction (4) takes place under similiar temperatures and ratios. If a solvent is used the temperature of reaction will vary accordingly. Usually atmospheric or ambient pressure is used, however, higher or lower pressures may be used, if desired. The times of reaction will, or course, vary primarily with the temperature and pressure, etc, used. Any suitable hydrocarbon solvent, such as xylene or toluene may be used.

The base lubricants which are useful with the additives of this invention may be any oil of lubricating viscosity, whether natural, i.e., mineral, or snythetic.

The additives may be therefore incorporated into any suitable lubricating media which comprises oils of lubricating viscosity, mineral or synthetic; or mixtures of mineral and synthetic or greases in which the aforementioned oils are employed as a vehicle or into such functional fluids as hydraulic fluids, brake fluids, power transmission fluids and the like. In general, mineral oils and/or synthetic oils, employed as the lubricant oil, or grease vehicle may be of any suitable lubricating viscosity range, as for example, from about 45 SSU at $100°$ F. to about 6000 SSU at $100°$ F., and, preferably, from about 50 to about 250 SSU at $210°$ F. These oils may have viscosity indices from about 70 to about 95 preferred. The average molecular weight of these oils may range from about 250 to about 800. Where the lubricant is to be employed in the form of a grease, the lubricating oil is generally employed in an amount sufficient to balance the total grease composition.

In instances where synthetic oil, or synthetic oils are employed as the vehicle for the grease in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylolpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxyl phenyl) ether, phenoxy phenylethers, etc.

Fully formulated lubricating oils may include therein a variety of additives (for their known purpose) such as dispersants, detergents, inhibitors, antiwear agents, antioxidant, antifoam, pour depressant and other additives including metallic or non-metallic phenates, sulfonates and zinc dithiophosphates.

When high temperature stability is not a requirement of the finished grease, mineral oils having a viscosity of at least 40 SSU at $150°$ F., and particularly those falling within the range from about 60 SSU to about 6,000 SSU at $100°$ F. may be employed. The lubricating vehicles of the improved greases of the present invention, containing the above described additives, are combined with a grease forming quantity of a thickening agent. For this purpose, a wide variety of materials may be dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickeners may be employed which do not melt and dissolve when used at the required temperature within a particular environment; soap thickeners such as metallic (lithium or calcium) soaps including hydroxy stearate and/or stearate soaps can be used however, in all other respects, any material which is normally employed for thickening or gelling hydrocarbon fluids or forming greases in accordance with the present invention.

Included among the preferred thickening agents are those containing at least a portion of alkali metal, alkaline earth metal or amine soaps of hydroxyl-containing fatty acids, fatty glycerides and fatty esters having from 12 to about 30 carbon atoms per molecule. The metals are typified by sodium, lithium, calcium and barium. Preferred is lithium. Preferred members among these acids and fatty materials are 12-hydroxystearic acid and glycerides containing 12-hydroxystearates, 14-hydroxystearic acid, 16-hydroxystearic acid and 6-hydroxystearic acid.

Other thickening agents include salt and salt-soap complexes such as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,066), and calcium salts and soaps of low-, intermediate-and high molecular weight acids and of nut oil acids.

As has been disclosed hereinabove, the reaction products are useful as multifunctional antiwear/antioxidant/antirust agents. They are added to the lubricating medium in amounts sufficient to impart such properties to the lubricant. More particularly, such properties will be imparted to the lubricant by adding from about 0.001% to about 10% by weight, preferably from about 0.001% to about 3%, of the neat product. These novel composition described do not contain any potentially undesirable chlorides.

The following examples are exemplary only and are not intended as limitations.

EXAMPLES

EXAMPLE 1

Propoxylated Di-(2-ethylhexyl)phosphorodithioic acid (O,O-di-2-ethylhexyl-S-(2-hydroxypropyl)phosphorodithioate)

Approximately 708.6 grams of di-(2-ethylhexyl) phosphorodithioic acid (commercially obtained from Stauffer Chemical Company) was charged into a 1-liter stirred reactor equipped with a condenser and a thermometer. Approximately 116.2 grams of propylene oxide (equal molar) was slowly added over a course of two hours. The reaction temperture was controlled at or below 40° C. by using ice-water bath for cooling. At the end of the addition, the reaction mixture changed its color from dark-greenish to light yellowish. It weighted approximately 825 grams.

EXAMPLE 2

[(O,O-di-2-ethlhexyl-S-(2-hydroxypropyl)phosphorodithioate) substituted dodecenyl succinic acid ester]

Approximately 412.5 grams of the above product of Example 1, and 266.0 grams (1.0 mole) of dodecenyl succinic anhydride were mixed together in a 1-liter, 4-neck reactor equipped with thermometer, condenser, agitator and nitrogen sparger. This mixture was heated at 82°±2° C. over a course of six hours and at the end of the reaction, a yellow, viscous liquid was recovered.

EXAMPLE 3

O,O-di-(2-ethylhexyl)-S-(2-hydroxypropyl)phosphorodithioate-Dodecenyl succinic anhydride-Aniline adduct Approximately 329 grams of the above product of Example 2 (0.485 mole), 45.6 grams of aniline (0.49 mole), and 150 ml of toluene were charged to a reaction vessel. This mixture was heated up and refluxed at 115°±2° C. over the course of ten hours. A total amount of 4 ml of water was collected in the Dean Stark trap. At the end of the reaction, the volatiles were removed by vacuum distillation, and the viscous product was diluted with about 100 grams of mineral oil diluent for improving fluidity and easy handling. Then the crude product was further filtered to remove some insoluble solids and this gave 457 grams of brownish liquid.

EXAMPLE 4

The procedure of Example 3 was followed with the following exception: the molar ratio of Example 2 versus aniline was 2:1 instead of 1:1, and no diuent oil was used.

EXAMPLE 5

O,O-di-4-methyl-2-pentyl-S-(2-hydroxypropyl)phosphorodithioate

The procedure of Example 1 was followed with only one exception: equimolar di-(4-methyl-2-pentyl)phosphorodithioic acid was used instead of di-(2-ethylhexyl)phosphorodithioic acid.

EXAMPLE 6

O,O-di-2-butyl-S-(2-hydroxypropyl)phosphorodithioate

The procedure of Example 1 was followed with one exception: equimolar di-2-butyl phosophorodithioic acid was used instead of di-(2-ethylhexyl)phosophorodithioic acid.

EXAMPLE 7

O,O-di-2-methyl-1-propyl-S-(2-hydroxypropyl)phosphorodithioate

The procedure of Example 1 was followed with one exception: equimolar di-2-methyl-1-propyl phosophorodithioic acid was used instead of di-(2-ethylhexyl)phosphorodithioic acid.

EXAMPLE 8

[O,O-di-2-methyl-1-propyl-S-(2-hydroxypropyl)phosphorodithioate) substituted dodecenyl succinic acid ester]

The procedure of Example 2 was followed with the following exceptions: equimolar product of Example 7 was used instead of product of Example 1. In addition, catalytic amounts of hydrochloric acid and para-toluene sulfonic acid were used to facilitate the reaction.

EXAMPLE 9

The procedure of Example 4 was followed with following exceptions: equimolar products of Example 8 and Primene 81R ($C_{12}$ to $C_{14}$ mixed alkylamines) obtained from Rohn & Haas Chemical Company were used instead of products of Example 2 and aniline.

EXAMPLE 10

The procedure of Example 9 was followed with following exceptions: bis(2-ethylhexyl)amine was used instead of Primene 81R, obtained from Rohn & Haas Chemical Company and catalytic amount of dimethylaminopyridine was also used.

EXAMPLE 11

Equimolar amounts of the product of Example 5, dodecenyl succinic ahnydride and 2-butanol were reacted in a similar procedure as described in Examples 3,9, 10.

EXAMPLE 12

The procedure of Example 11 was followed with one exception: dibutylamine was used instead of 2-butanol.

EXAMPLE 13

The procedure of Example 12 was followed with the following exception: catalytic amount of triethylamine was used in the reaction of the product of Example 5 with dodecenyl succinic anhydride, and Ethomeen C/12 (bis-2-hydroxyethyl cocoamine) obtained from Armak Corporation was used instead of dibutylamine in the subsequent reaction.

EXAMPLE 14

The procedures of Examples 2 and 4 were followed with the following exception: a catalytic amount of triethylamine was used in the reaction of Example 2, and Jeffamine D-230 (polyoxyalkylene amine available from Texaco Chemical Company) was used instead of aniline in the reaction of Example 4.

The products of the above Examples were blended into mineral oils and evaluated for antiwear performance using the Four-Ball Test (ASTM Method D-2266, Table 1).

TABLE 1

Four-Ball Wear Test
(60 kg, 2000 rpm, 30 min., 200° F.)

| Item | Wear Scar Diameter (mm) |
|---|---|
| Base Oil (80% solvent refined paraffinic bright oil, 20% solvent refined paraffinic neutral oil) | 4.08 |
| 1% of Example 4 in the above base oil | 0.88 |
| 1% of Example 9 in the above base oil | 0.61 |
| 1% of Example 10 in the above base oil | 0.71 |
| 1% of Example 11 in the above base oil | 0.64 |
| 1% of Example 12 in the above base oil | 0.64 |
| 1% of Example 13 in the above base oil | 0.54 |
| 1% of Example 14 in the above base oil | 0.70 |

The additive of Example 4 was also blended into calcium complex greases and evaluated for antiwear-/EP properties using the Optimol SRV Friction and Wear Test (Table 2, Test purposes: evaluate friction, wear and breakaway torque characteristics of lubricants and materials under high-speed oscillation).

The grease incorporating additive amounts of Example 4 was subjected to an Optimol SRV stepload test under conditions recommended by Optimol Lubricants, Inc. and used by Automotive Manufacturers such as General Motors for lubricant evaluation. This method was also specified by the U.S. Air Force Laboratories Test Procedure of Mar. 6, 1985. In the test, a 10 mm steel ball is oscillated under load increments of 100 newtons on a lapped steel disc lubricated with the grease being tested until seizure occurs.

TABLE 2

Optimol SRV Test
(50° C., 0.5 mm stroke, 60 minutes, 300 Newton Load)

| Item | Wear Scar Diameter (mm) |
|---|---|
| Base Grease (formulated calcium complex mineral oil based grease) | 0.61 |
| 2% Example 4 in above base grease | 0.49 |

The product of Example 4 was also blended into synthetic oils and evaluated for antioxidant performance by Catalytic Oxidation Test at 325° F. for 40 hours (Table 3).

CATALYTIC OXIDATION TEST

The test lubricant composition is subjected to a stream of air which is bubbled through the composition at a rate of five liters per hour at the specified temperature for the required number of hours. Present in the composition (comprising a 150 second solvent refined paraffinic bright oil) in addition to the additive compound were metals commonly used as materials to construct engines namely:

(a) 15.6 square inch of sand-blasted iron wire;
(b) 0.78 square inch of polished copper wire;
(c) 0.87 square inch of polished aluminum wire; and
(d) 0.107 square inch of polished lead surface.

TABLE 3

Catalytic Oxidation Test
(40 hours at 325° F.)

| Item | % Change in Viscosity | Change in Acid Value | Slude Rating |
|---|---|---|---|
| Base Oil (mixed polyalphaolefin-derived (PAO) and ester synthetic oils) | 293 | 8.1 | Trace |
| 1% of Example 4 in above base oil | 50.9 | 6.2 | Nil |

As can be seen from the above test results, the products described exhibit considerable antiwear activity and antioxidation characteristics in lubricating oils and greases.

The use of additive concentrations of phosphorodithioate substituted carboxylic anhydride derived esters-/amides/amine salts in premium quality automotive and industrial lubricants will significantly enhance the stability, extend the service life, reduce the wear, and prevent the rust of the metal surface.

Although the present invention has been described with preferred embodiments, it is to be understood that modifications and variations may be utilized without departing from the spirit and scope of this invention, as those skilled in the art will readily understand. Such modifications and variations are considered to be within the purview and scope of the appended claims.

What is claimed is:

1. An improved composition comprising a major amount of an oil of lubricating viscosity or a grease prepared therefrom and a minor multifunctional antioxidant, antiwear and/or anticorrosion amount of an additive product of reaction comprising a phosphorodithioate substituted hydrocarbyl carboxylic anhydride-derived organic ester, amide or amine salt thereof selected from the group consisting of:

O,O-di-2-methyl-1-propyl-S-(2-hydroxypropyl)-phosphorodithioate-dodecenyl-succinic anhydride aniline adduct;

O,O-di-2-methyl-1-propyl-S-(2-hydroxypropyl)-phosphorodithioate-dodecenyl-succinic anhydride-mixed $C_{12}$-$C_{14}$ alkylamine adduct;

O,O-di-2-methyl-1-propyl-S-(2-hydroxypropyl)-phosphorodithioate-dodecenyl-succinic anhydride-bis(2-ethylhexyl) amine adduct;

O,O-di-4methyl-2-pentyl-S-(2-hydroxypropyl) phosphorodithioate-dodecenyl-succinic anhydride-2-butanol adduct;

O,O-di-4-methyl-2-pentyl-S-(2-hydroxypropyl)-phosphorodithioate-dodecenyl-succinic anhydride-dibutyl amine adduct;

O,O-di-4-methyl-2-pentyl-S-(2-hydroxypropyl)-phosphorodithioate-dodecenyl-succinic anhydride-(bis-2-hydroxethyl cocoamine) adduct;

O,O-di-4-methyl-2-pentyl-S-(2-hydroxypropyl)-phosphorodithioate-dodecenyl-succinic anhydride-polyoxyalkylene amine adduct and O,O-di-(2-ethylhexyl-S-(2-hydroxypropyl)-phosphorodithioate-dodecenyl succinic anhydride-aniline adduct.

2. The composition of claim 1 wherein said product of reaction is O,O-di-2-methyl-1-propyl-S-(2-hydroxypropyl)-phosphorodithioate-dodecenyl-succinic anhydride aniline adduct.

3. The composition of claim 1 wherein said product of reaction is O,O-di-2-methyl-1-propyl-S-(2-hydroxylpropyl)-phosphorodithioate-dodecenyl-succinic ahnydride-mixed $C_{12}$–$C_{14}$ alkylamine adduct.

4. The composition of claim 1 wherein said product of reaction is O,O-di-2-methyl-1-propyl-S-(2-hydroxypropyl, phosphorodithioate-dodecenyl succinic anhydride-bis(2-ethylhexyl) amine adduct.

5. The composition of claim 1 wherein said product of reaction is O,O-di-4-methyl-2-pentyl-S-(2-hydroxypropyl)-phosphorodithioate-dodecenyl succinic anhydride-2-butanol adduct.

6. The composition of claim 1 wherein said product of reaction is O,O-di-4-methyl-2-pentyl-S-(2-hydroxypropyl)-phosphorodithioate-dodecenyl succinic anhydride-dibutyl amine adduct.

7. The composition of claim 1 wherein said product of reaction is O,O-di-4-methyl-2-pentyl-S-(2-hydroxypropyl)-phosphorodithioate-dodecenyl succinic anhydride-(bis-2-hydroxyethyl cocoamine) adduct.

8. The composition of claim 1 wherein said product of reaction is O,O-di-4-methyl-2-pentyl-S-(2-hydroxypropyl)-phosphorodithioate-dodecenyl succinic anhydride-polyoxyalkylene amine adduct.

9. The composition of claim 1 wherein said oil of lubricating viscosity is selected from mineral oils, synthetic oils or mixtures thereof.

10. The composition of claim 9 wherein said oil is a mineral oil.

11. The composition of claim 9 wherein said oil is a synthetic oil.

12. The composition of claim 9 wherein said oil is a mixture of synthetic and mineral oils.

13. The composition of claim 1 wherein said composition is a grease composition prepared from any one of (1) mineral oils, (2) synthetic oils or (3) a mixture of mineral and synthetic oils.

14. The composition of claim 13 wherein said grease is a calcium complex grease.

15. The composition of claim 14 wherein said phosphorodithioate substituted anhydride, ester, amide or amine salt thereof is O,O-di-(2-ethylhexyl)-S-(2-hydroxypropyl)-phoshorodithioate-dodecenyl succinic anhydride-aniline adduct.

* * * * *